United States Patent [19]

Hasebe et al.

[11] Patent Number: 4,915,116

[45] Date of Patent: Apr. 10, 1990

[54] FINGERTIP PULSE WAVE SENSOR

[75] Inventors: Norboru Hasebe, Kunitachi; Shoji Ito, Tokyo, both of Japan

[73] Assignee: Misawa Homes Institute of Research & Development, Tokyo, Japan

[21] Appl. No.: 329,535

[22] Filed: Mar. 28, 1989

[30] Foreign Application Priority Data

| Jul. 6, 1988 | [JP] | Japan | 63-1667890 |
| Sep. 24, 1988 | [JP] | Japan | 63-237533 |
| Sep. 24, 1988 | [JP] | Japan | 63-237534 |
| Sep. 24, 1988 | [JP] | Japan | 63-237536 |

[51] Int. Cl.$^4$ .............................................. A61B 5/02
[52] U.S. Cl. .................................... 128/666; 128/687
[58] Field of Search .............................. 128/687–689, 128/691, 666, 633

[56] References Cited

U.S. PATENT DOCUMENTS

| 2,684,671 | 7/1954 | Mendelsohn | 128/687 X |
| 2,790,438 | 4/1957 | Taplin et al. | 128/633 |
| 3,154,066 | 10/1964 | Grindheim et al. | 128/687 |
| 3,628,525 | 12/1971 | Polanyi et al. | 128/633 |
| 3,841,314 | 10/1974 | Page | 128/666 |
| 4,129,124 | 12/1978 | Thalmann | 128/666 |
| 4,332,258 | 6/1982 | Arai et al. | 128/666 |
| 4,685,464 | 8/1987 | Goldberger et al. | 128/687 X |
| 4,838,277 | 6/1989 | Affeldt et al. | 128/687 X |

*Primary Examiner*—Francis Jaworski
*Attorney, Agent, or Firm*—Hoffmann & Baron

[57] ABSTRACT

A fingertip pulse wave sensor includes a fingertip supporting base having either a nail supporting surface or a fingertip cushion supporting surface, and a slider having the other of the nail supporting surface and the fingertip cushion supporting surface. The slider is guided on the fingertip supporting base in such a manner as to be slidable in the direction in which it is moved away from or toward the fingertip supporting base. The slider is urged in the direction in which it is moved toward the fingertip supporting base by an elastic body which is capable of applying a substantially fixed amount of pressure with respect to the variations in the slide stroke in the direction in which the slider is moved away from the fingertip supporting base which occur when different fingertips are set. The fingertip pulse wave sensor also includes a light-emitting element disposed in one of the nail supporting surfaces and the fingertip cushion supporting surface, and a light-receiving element disposed on the other of the nail supporting surface and the fingertip cushion supporting surface.

7 Claims, 5 Drawing Sheets

FINGERTIP PULSE WAVE SENSOR

BACKGROUND OF THE INVENTION

1. Field of the Invention:

The present invention relates to a fingertip pulse wave sensor for detecting changes in the volume of a blood vessel in a fingertip held between a light-emitting element and a light-receiving element, in which the changes are caused by pulsation and detected as electrical signals produced in response to changes in the intensity of the light transmitted through the fingertip.

2. Description of the Related Art:

FIG. 16 shows a conventional fingertip pulse wave sensor of the above-described type. This fingertip pulse wave sensor includes generally, a pad 2, a pad 3, and a plate spring 4. Pad includes either a light-receiving element or a light-emitting element buried therein which is disposed near the nail of a fingertip 1. Pad 3 has the other of the light-receiving and light-emitting elements buried therein and is disposed near a fingertip cushion 1a in such a manner as to face the pad 2. The plate spring 4 has a substantially U-shaped form, and is mounted on the rear surface of the pad 3 so as to hold the fingertip 1 between the two pads 2 and 3 under pressure.

With this arrangement, although the fingertip can be elastically held in place in spite of the variations naturally occurring in the shape of the fingertips of different individuals or any irregularities in the top dead point of the plate spring 4 employed, these variations or irregularities serve to cause variations in the amount of pressure applied to the finger to a considerable extent. For example, in the case of a spring designed to provide a force that will press a fingertip with a deflection of 3 mm, if a deflection of 6 mm is caused (e.g. due to differences in the shape of different individuals' fingertips or irregularities in the top dead point of the spring employed), it is possible that the pressure applied to the fingertip will be completely different. Excessive pressure exerted on a portion to be measured, increases the amount of blood in the venula of the fingertip, this blood being returned to the associated vein. This has an effect on the waveform of a pulse produced during arterial pulse wave detection at the fingertip.

This is undesirable in terms of the measurement precision in a plethysmograph which is designed to estimate the form of a arterial pulse waveform in its detected state. This greatly affects the results of measurements obtained using an "acceleration-type" fingertip pulse wave detector which must be able to non-invasively monitor the state of a peripheral circle by converting the waveform detected to an acceleration curve. This waveform conversion is achieved by differentiating twice the detected waveform with respect to the time. Such requirements make the use of such acceleration-type fingertip pulse wave detectors in clinical applications, impossible.

SUMMARY OF THE INVENTION

Accordingly, an object of the present invention is to provide a fingertip pulse wave sensor which is capable of detecting a fingertip pulse wave in a consistent manner and with a high degree of accuracy in spite of differences occurring in the shape of fingertips among different individuals.

In order to achieve this object, the present invention provides a fingertip pulse wave sensor which is based on the confirmation that application of a certain amount of pressure is inevitable for stable pulse wave detection. The fingertip pulse wave sensor comprises a slider and an elastic body. The slider has either a fingertip cushion supporting surface or a fingernail supporting surface or both of them, which respectively incorporate transmitting and receiving photoelectric elements disposed in opposed relationship. The slider is adapted to slide in the direction in which these surfaces are moved away from or toward each other. The elastic body is provided for urging the slider in the direction in which the surfaces are moved toward each other. The elastic body is capable of applying a substantially fixed amount of pressure to a fingertip in spite of the variations in the slide stroke of the slider in the direction in which the surfaces are moved away from each other. Notably, the variations in the slide stroke are caused by the differences in the fingertips held on the surface. The fingertip pulse wave sensor of the present invention enables adoption of various types of spring structure which are capable of maintaining the pressure applied at a fixed value, unlike a plate spring which directly presses against a fingertip.

Present invention allows a fingertip to be gripped between photoelectric elements under a substantially fixed yet appropriate pressure which is sufficient to keep the fingertip in place and yet not to compress blood vessel to the extent of affecting the measurement accuracy. This enables detection of a stable pulse waveform signal accurately corresponding to changes in the volume of a blood vessel. In particular, application of the present invention to an acceleration pulse wave detector which requires that a stable pulse waveform be detected with a high degree of accuracy, enables highly reliable monitoring of the conditions of peripheral circulation. Consequentially, it is expected that this will open the way to use of the acceleration-type fingertip pulse wave detectors in clinical applications, including prevention and cure of degenerative diseases, such as arterial sclerosis, caused by circulatory disorders.

DETAILED DESCRIPTION OF THE PREFERRED EMBODIMENTS

FIGS. 1 to 4 show a first embodiment of the present invention.

Figure 1:
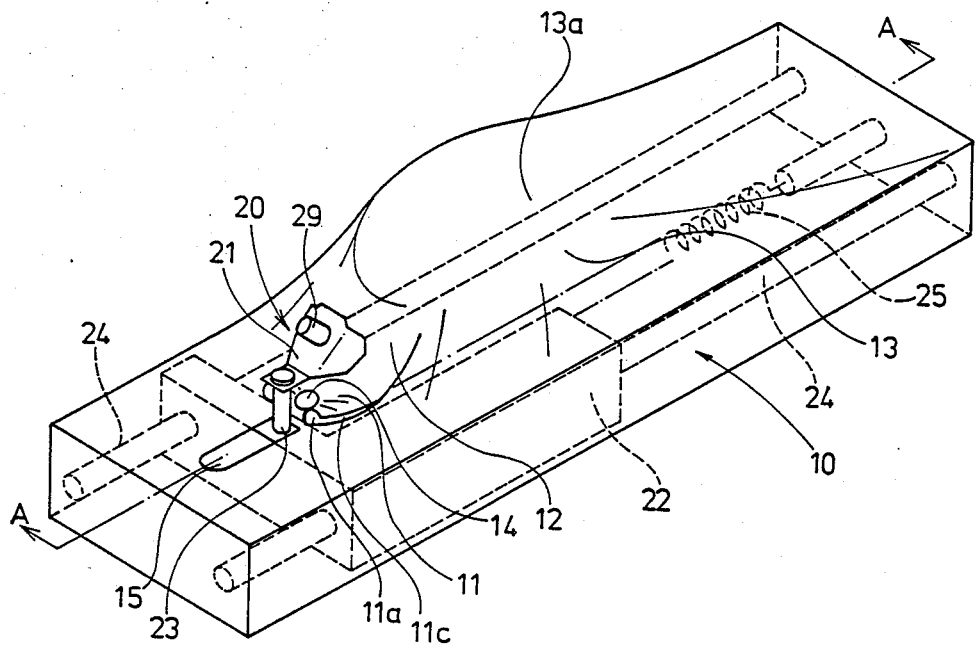
FIG. 1 is a prespective view of a fingertip pulse wave sensor, showing a first embodiment of the present invention.
Figure 2:
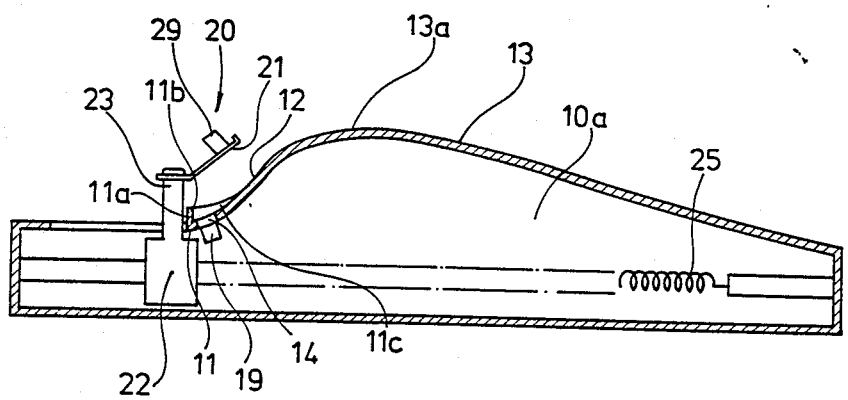
FIG. 2 is a section taken along the line 2—2 of FIG. 1.
Figure 3A:
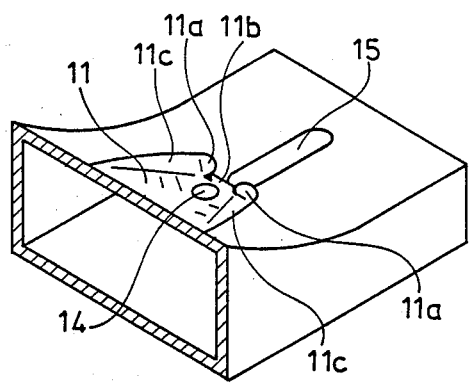
FIG. 3a is a perspective view of a fingertip cushion supporting portion of the sensor of FIG. 1.
Figure 3B:
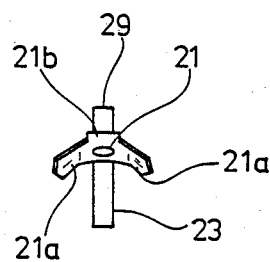
FIG. 3b is a front view of a fingernail contact surface of the sensor of FIG. 1.

The fingertip pulse wave sensor shown in FIG. 1 includes a fingertip supporting base 10 of a fixed type which does not move in a state when a fingertip is set thereon. The fingertip supporting base 10 includes a fingertip guide surface 12, and a rising surface 13. The fingertip supporting base 10 has on its surface, a fingertip cushion supporting surface 11 which is slightly inclined with respect to the bottom surface of the fingertip supporting base 10. The fingertip guide surface 12 has a steeper slope than that of the fingertip cushion supporting surface 11. The rising surface 13 rises in a form that allows the palm of a hand to be supported thereon. As illustrated in the drawings these surfaces 11, 12 and 13 are formed in that order with the fingertip cushion supporting surface 11 located at the forward end front.

The fingertip cushion supporting surface 11 has a central flat portion and it also has side walls 11c which come closer to each other as they approach the forward end of the fingertip supporting base. The periphery of the fingertip cushion supporting surface, forms a curved surface which rises as it approaches the side edges. A circular through-hole 14 is formed in the fingertip cushion supporting surface 11, on which a fingertip cushion 1a is placed so that no pressure is applied to this central portion of the fingertip cushion 1a. The fingertip cushion supporting surface 11 also has stoppers 11a which protrude substantially in the vertical direction at the forward end of the fingertip cushion supporting surface 11, so as to press against the forward end of a fingertip resting thereon. A notch 11b is formed between the stoppers 11a at such a position that it faces the fingernail of the finger resting in place so that a long nail will not get caught (see FIG. 3a).

The fingertip guide surface 12 has a steeper slope to cope with the standard shape of the finger cushion of, for example, a forefinger between the first joint and the second joint thereof, when the forefinger is set with the fingertip cushion 1a placed on the fingertip cushion supporting surface 11 in a relaxed state. Similarly, the rising surface 13 is curved to assume a form in which a central portion 13a is highest. Notably, a portion of the subject's finger (i.e. in the vicinity of the third joint) resting in a relaxed state, is generally placed on the central portion 13a.

A slider 20, adapted to press against the subject's fingernail, comprises guide rods 24, slider block 22, an arm 23, and a nail contact surface 21. Guide rods 24 run in a hollow portion 10a of the fingertip supporting base 10 at the two sides thereof parallel to the bottom surface of the fingertip supporting base 10. Slider block 22 is slidably supported on the guide rods 24 and the arm 23 protrudes vertically from the slider block 22 past an elongated hole 15. The nail contact surface 21 on the other hand, is held on the arm 23 and is adapted to be brought into contact with the fingernail. The nail contact surface 21 is inclined at an angle equivalent to the standard inclination angle formed by the nail of a finger held in a relaxed state, with the fingertip cushion 1a being placed on the fingertip cushion supporting surface 11, that is, it is inclined such as to be substantially parallel with the fingertip guide surface 12, so that it makes contact with the nail surface. This feature is achieved by the sliding of the nail contact surface 21 in the forward direction by a distance proportional to the thickness of a fingertip. The nail contact surface 21 has curved side walls 21a at its two sides, and a curved guide surface 21b at the front thereof (see FIG. 3b).

Between the slide block 22 and the rear end of the hollow portion 19a thereof, is disposed a helical spring 25 which is sufficiently long with respect to the slide stroke of the slider 20 which will vary in accordance wit differences in the fingertip among different individuals. For example, the helical spring 25 can be set so as to have a length of 100 mm when it provides a force strong enough to hold a fingertip in place, and yet not so strong as to block the flow of blood in the portion being measured, and such that, when the slide stroke is 5 mm, any variation in the pressure applied to the fingertip is about 2% of the slide stroke. A light-emitting element 19 is disposed below the hole 45, and a light-receiving element 29 is buried in the central portion of the nail contact surface 21.

The operation of the thus-arranged fingertip pulse wave sensor will be described below.

Generally, the slider 20 is located such that the arm 23 thereof is at the rear end of the elongated hole 15.

Figure 4A:
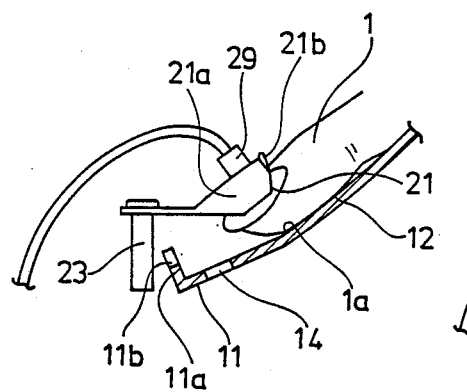
FIG. 4 is a side elevational view illustrating a state where a finger is set in the sensor of FIG. 1.
Figure 4B:
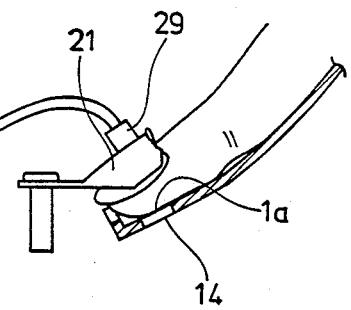

When measurement is to be conducted, the fingertip 1 is inserted between the fingertip guide surface 12 and the nail contact surface 21, as shown in FIG. 4a. This causes the slider 20 to slide forwardly. Next, as shown in FIG. 4b, the forward end of the finger 1 is advanced until it makes contact with the stoppers 11a. At this time, the fingertip is held in place by the nail contact surface 21 and the fingertip cushion supporting surface 11. Further, although the slide position of the slider 20 varies in accordance with the height of the nail of the finger inserted, the pressure applied to the nail is maintained at a substantially fixed and appropriate value because the helical spring 25 is sufficiently long with respect to any variations in the slide stroke of the spring. Thus, (i) no light which would disturb the measurement will be present, (ii) the fingertip 1 is constantly held in place in a stable condition, and (iii) no distortion occurs in the waveform of pulses due to excessive pressure being applied to the fingertip.

The light emitted from the light-emitting element 19 passes through the through-hole 14, is transmitted through the fingertip 1, and is made incident on the light-receiving element 29 located on the surface that faces the hole where it is converted to an electrical signal. The thus-produced signal representing precise changes in the volume of a blood vessel, is supplied to the body (not shown) of the fingertip pulse wave sensor. The accuracy with which the detection is conducted is particularly high, because the central portion of the finger cushion faces the hole and compression of the blood vessel in this portion of the fingertip to be measured is therefore avoided.

In this embodiment, a recess which extends in the longitudinal direction of the fingertip supporting base 10 may be formed in place of the through-hole 14. In that case, only a portion of the fingertip supporting base 10 that faces the photoelectric elements is drilled to form a through-hole. Further, the fingertip cushion supporting surface and the fingertip guide surface may be made to incline at the same angle.

Figure 5:
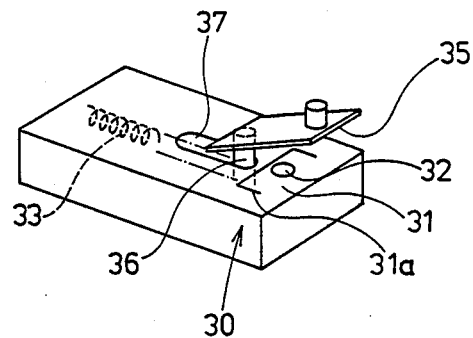
FIG. 5 is a perspective view of a fingertip pulse wave sensor, showing a second embodiment of the present invention.

FIG. 5 shows a second embodiment of the present invention. In this embodiment, a fingertip supporting base 30 is of the type which is held by one of the hands, unlike the fixed type of fingertip supporting base employed in the first embodiment. A fingertip cushion supporting surface 31 has a mark 31a formed thereon that indicates the position of the forward end of the fingertip, this being provided in place of the stoppers. A through-hole formed in the fingertip cushion supporting surface 31 does not function as a recess in the manner of the through-hole in the first embodiment, but instead, a light-transmitting window 32 is fitted thereinto. A slider 36 provided with a nail contact surface 35, is provided on the fingertip supporting base 30 in such a manner as to be slidable along an elongated hole 37 parallel to the fingertip cushion supporting surface 31. The slider 36 is urged rearwardly by a compression spring 33 which acts as an elastic body. A compact and simple structure such as that described above, also ensures that the pressure applied to the fingertip by the slider 36 is substantially constant. This enables highly reliable detection of a pulse wave regardless of differences in the shape of different individuals' fingertips.

Figure 6:
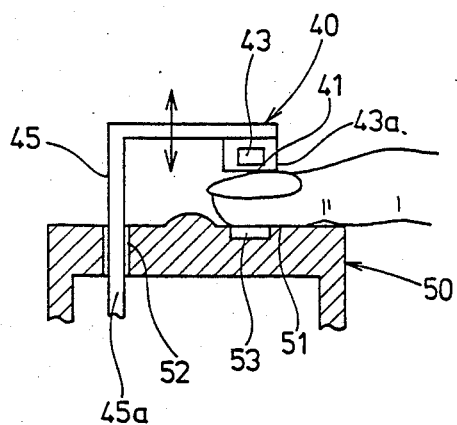
FIG. 6 is a cross-sectional view of the central portion of a fingertip pulse wave sensor, showing a third embodiment of the present invention.

FIG. 6 shows a third embodiment of the present invention. In this embodiment, a fingertip supporting base 50 has a horizontal fingertip cushion supporting surface 51 with a light-receiving element 53 buried therein. It also has a vertical guide hole 52 formed therein. An L-shaped slider 40 is provided with a pad 43a with a light-emitting element 43 buried therein. The front surface of the pad 43a forms a nail contact surface 41. A slider rod 45 of the slider 40 is guided through the guide hole 52. At a lower end 45a of this slider rod 45 is disposed an elastic body (not shown) which is capable of maintaining the pressure applied to a fingertip at a constant value with respect to the variations in the slide stroke. The following devices may be used as the elastic body: a helical spring having a sufficient length such as that described above; an air spring chamber having a sufficiently large volume with respect to variations in the changes in the volume caused by the slide of the slider; a balloon; and a constant load spring. In this embodiment, the optical path of the photoelectric elements 53 and 43 is identical with the direction in which the slider slides, and the slider thus slides along the optical path by a distance corresponding to the thickness of a finger held between the photoelectric elements.

Figure 7:
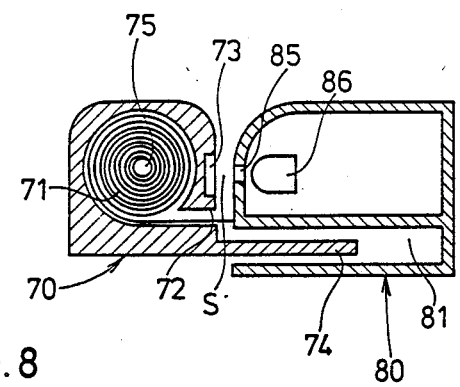
FIG. 7 is a cross-sectional view of the central portion of a fingertip pulse wave sensor, showing a fourth embodiment of the present invention.
Figure 8:
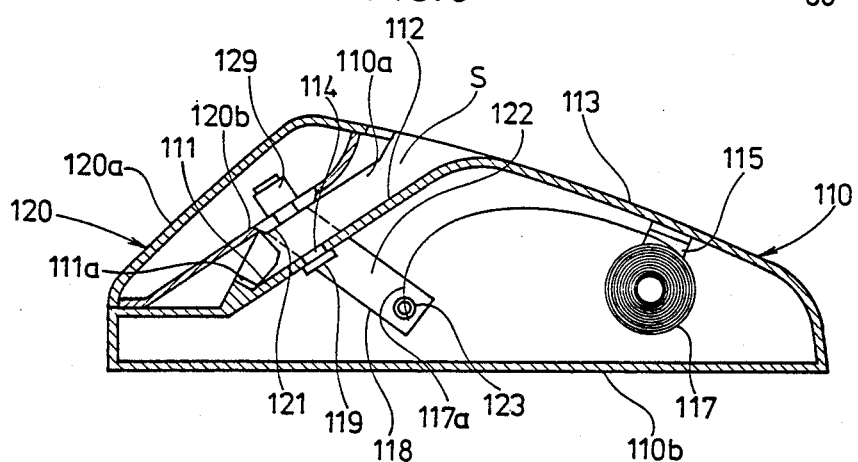
FIG. 8 is a cross-sectional view of the central portion of a fingertip pulse wave sensor, showing a fifth embodiment of the present invention.

FIG. 7 shows a fourth embodiment of the present invention which employs a constant load spring as an elastic body. In this embodiment, a slider 70 having the form of casing, has a nail contact surface 72 with either of photoelectric elements 73 buried therein. It also has a sliding plate 74 which protrudes from the bottom portion of the slider 70. A fingertip supporting base 80 has a fingertip cushion supporting surface 85. The sliding plate 74 is guided in a guide groove 81 formed in the fingertip supporting base 80. The slider 70 accommodates a known constant-load spiral spring 71 which acts as a constant-load spring and which is capable of maintaining a winding force at a constant value with respect to variations in the length of the spring being unwound. The inner end of the spiral spring 71 is pressed onto a rotary shaft 75 rotatably mounted on the wall surface of the slider 70 by virtue of the elasticity of the spring, and the outer end of the spring is passed through a small hole formed in the slider and is fixed to the fingertip supporting base 80. Once a fingertip is inserted in a gap, S, formed between the photoelectric elements 73 and 86, the slider is caused to slide along the optical path of the photoelectric elements by a distance corresponding to the thickness of the fingertip inserted. At this time, the constant-load spiral spring 71 is unwound against the winding force thereof. The fingertip pulse wave sensor of this embodiment is capable of maintaining the pressure exerted on the fingertip at a constant value, although it is small in size. It may be constructed as a fixed type or a hand-held type which is held by a hand other than a hand being measured.

FIGS. 8 to 11 show a fifth embodiment of the present invention which employs a constant-load spiral spring of the above-described type.

This fingertip pulse wave sensor includes a fingertip supporting base 110 of the type which is fixed on a flat surface. The fingertip supporting base 110 has on its surface, a fingertip cushion supporting surface 111, a fingertip guide surface 112, and a rising surface 113 The fingertip cushion supporting surface 111 is slanted with respect to the bottom surface of the fingertip supporting base in order to cope with the standard shape of a fingertip cushion placed thereon in a relaxed state. The fingertip guide surface 112 is inclined by the same angle as that of the inclination of the fingertip cushion supporting surface 111 in order to cope with the shape of the finger cushion of the finger located between the first and second joints. The rising surface 113 is curved to assume a form, in which a portion of the fingertip that is in the vicinity of the third joint, rests on the highest spot of the rising surface 113. Guide walls 110a are formed at the two sides of the fingertip cushion supporting surface 111 and the fingertip guide surface 112 at an interval which is slightly broader than the standard width of the finger.

A circular through-hole 114 is formed in the fingertip cushion supporting surface 111 so that the central portion of the finger cushion escapes therethrough. A stopper 111a, which is curved to cope with the shape of the forward end of the fingertip and which is low enough not to catch the long nail, is formed at the forward end of the fingertip cushion supporting surface 111.

A slider 120 adapted to press against the fingernail has a cover 120a, and an inner panel 120b of the cover 120a has a nail contact surface 121 which makes contact with the fingernail. A slider arm 122 is mounted on each of the two sides of the slider 120 slantingly with respect to a bottom surface 110b in such a way as to be slidable in a guide groove 118 formed in each of the two side walls of the fingertip supporting base 110. A light-emitting element 119 is mounted on the rear surface of the fingertip cushion supporting surface 111 at a position where it faces the through-hole 114, and a light-receiving element 120 is mounted on the nail contact surface 121 at a position where it faces a through-hole. The slider arms 122 are inclined at an angle slightly smaller than that of the inclination of the optical path of the photoelectric elements. When the cover 120a is in a closed state, the nail contact surface 121 is separated from the fingertip cushion supporting surface 111 by a distance which is slightly smaller than the standard thickness of the fingertip so as to form a gap S therebetween which becomes wider in the direction of the thickness of the fingertip as it approaches the upper end thereof.

Figure 9:
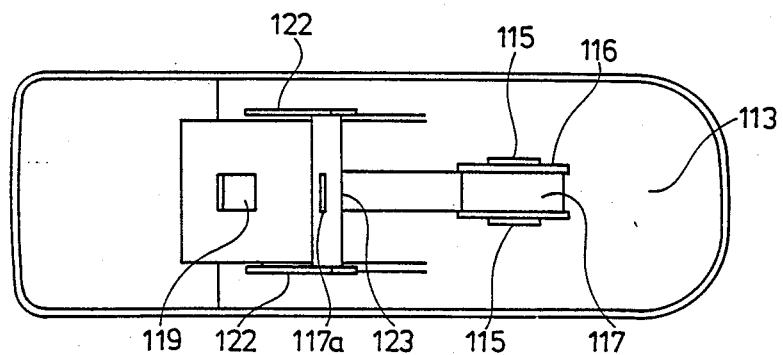
FIG. 9 is a bottom view of the fingertip pulse wave sensor of FIG. 8 shown in a state wherein a rear lid is removed.
Figure 10:
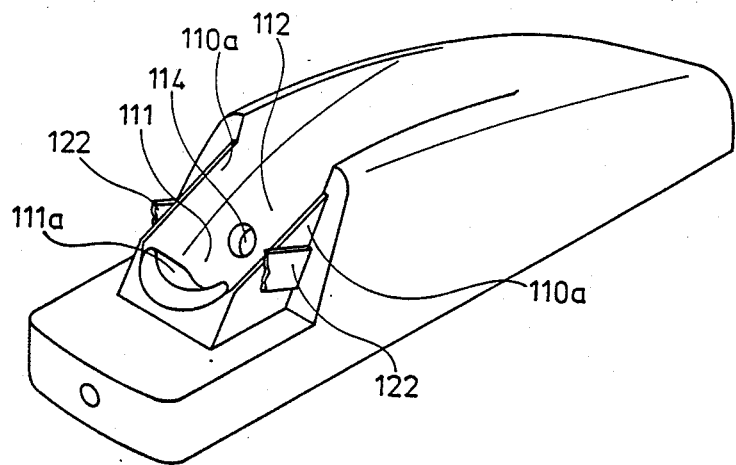
FIG. 10 is a perspective view of the fingertip pulse wave sensor of FIG. 8 which excludes a slider portion.
Figure 11:
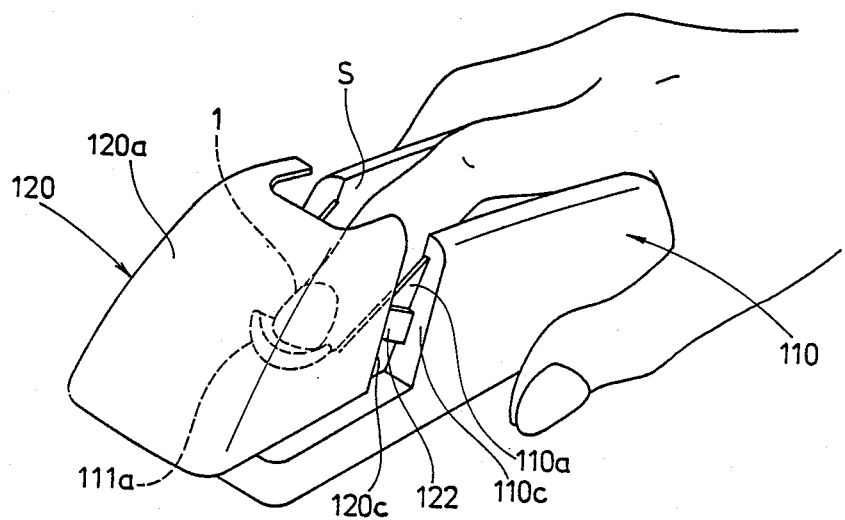
FIG. 11 is a perspective view of the fingertip pulse wave sensor of FIG. 8, shown a state wherein a fingertip is inserted into the sensor.

The lower ends of the slider arms 122 are connected by a rod 123, as shown in FIG. 9. A constant-load sprial spring 117 is accommodated below the rising surface 113, that is, in the interior of the fingertip supporting base 110 near the rear end thereof. The inner end of the sprial spring 117 is pressed onto a bobbin 116 rotatably mounted on arms 115 hanging from the rising surface 113 by virtue of the elasticity thereof, and an outer end 117 a thereof is fixed to the rod 123.

Generally, the slider 120 is located at a position where rear edges 120c thereof are in contact with front edges 110C of the fingertip supporting base 110, that is, it is located at a closed position. When measurement is to be conducted, a fingertip 1 is inserted into the gap S and is caused to slide along the fingertip guide surface 112. The fingertip 1 is then advanced until the forward end thereof abuts against the stopper 111a in a state wherein the finger cushion is in contact with the fingertip cushion supporting surface. This moves the nail contact surface 121 away from the fingertip cushion supporting surface 111 by a distance corresponding to the height of the nail. However, the pressure applied to the nail by the nail contact surface 121 is maintained at a substantially fixed and appropriate value, and no light which would disturb the measurement will be present. Further, the fingertip 1 is constantly held in place on the fingertip cushion supporting surface 111 in a stable condition, and no distortion occurs in the waveform of pulses due to excessive pressure being applied to the nail.

The light emitted from the light-emitting element 119 passes through the hole 114, is transmitted through the fingertip 1, and is then received by the light-receiving element 129 located at a position that opposes the hole 114 where it is converted to an electrical signal. The thus-prepared signal representing the precise changes in the volume of a blood vessel, is supplied to the body (not shown) of the fingertip pulse wave sensor.

In this embodiment, the constant-load spiral spring 117 may also be arranged such that the inner end thereof is pressed onto a rod 123 which is formed as a rotary shaft, and that the outer end of the spring is fixed to the fingertip supporting base 110. This also enables the spring to be unwound by the movement of the slider 120. Further, if the height of the fingertip supporting base may be able to be made larger, the direction in which the slider slides can be made identical with the optical path. The fingertip guide surface may also be made steeper than the fingertip cushion supporting surface so that the finger cushion of the finger located between the first and second joints, can be completely brought into contact with the fingertip guide surface when it is rested thereon.

Figure 12:
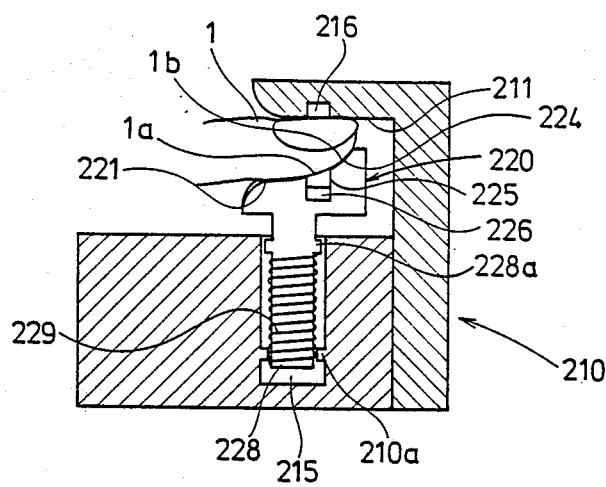
FIG. 12 is a cross-sectional view of the central portion of a fingertip pulse wave sensor, showing a sixth embodiment of the present invention.
Figure 13:
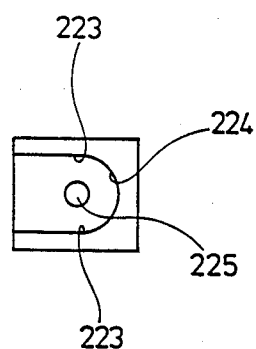
FIG. 13 is a plan view of a fingertip cushion supporting surface of the sensor of FIG. 12.

FIGS. 12 and 13 show a sixth embodiment of the present invention;

In this embodiment, a fingertip supporting base 210 has a nail supporting surface 211 with a light-emitting element 216 buried therein at the upper portion thereof. The fingertip supporting base 210 also has a guide groove 215. A cylindrical base 228 of a slider 220 is guided in this guide groove 215 in such a manner as to be slidable away from and toward the nail supporting surface 211. The slider 220 has a fingertip cushion supporting surface 221 that is generally separated from the nail supporting surface 211 by a distance slightly smaller than the standard thickness of the fingertip.

The fingertip cushion supporting surface 221 rises toward the front end thereof so as to cope with the standard shape of the finger cushion, the front end thereof forming a fingertip stopper 224, as shown in FIG. 13. The fingertip cushion supporting surface 221 has guide walls 223 at the two sides thereof which are separated at a distance slightly larger than the standard width of the fingertip 1. The central portion of the fingertip cushion supporting surface 221 is provided with a hole 225 which faces the finger cushion 1a, and a light-receiving element 226 is buried in the slider behind the hole 225.

A helical spring 229 is provided between a spring seat 228a provided at the upper portion of the base 228 and a spring seat 210a provided on the fingertip supporting base 210. This helical spring 229 is made sufficiently long with respect to variations in the stroke of the fingertip cushion supporting surface 221, which occur when the fingertip rests thereon, so as to maintain the pressure applied to the fingertip at a substantially fixed value, in spite of the variations in the thickness of the fingertip.

When measurement is to be conducted, the fingertip 1 is inserted between the fingertip cushion supporting surface 22 and the nail supporting surface 211. The fingertip 1 is then caused to slide in a state wherein the finger cushion 1a is in contact with the fingertip cushion supporting surface 221 until a forward end 1b thereof makes contact with the stopper 224. During the sliding of the fingertip, the slider 220 lowers. This allows the finger cushion 1a to be held in place on the fingertip cushion supporting surface 211. Further, since the helical spring 229 is sufficiently long as compared with the variations in the stroke thereof, the pressure applied by the helical spring can be maintained substantially at a substantially fixed and appropriate value. Furthermore, no light which would disturb measurement will be present, the fingertip can be held in place on the nail supporting surface 211 in stable condition, and no distortion occurs in the waveform of pulses due to excessive pressure being applied to the fingertip.

Figure 14:
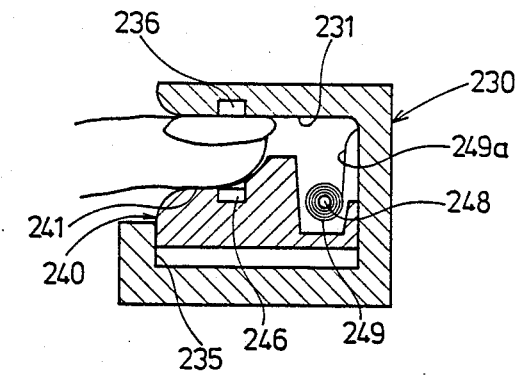
FIG. 14 is a cross-sectional view of the central portion of a fingertip pulse wave sensor, showing a seventh embodiment of the present invention.

FIG. 14 shows a seventh embodiment of the present invention. In this embodiment, a fingertip supporting base 230 has a nail supporting surface 231 with a light-emitting element 236 buried therein. It also had a guide groove 235 having a square cross-section. A slider 240 has a fingertip cushion supporting surface 241 with a light-receiving element 246 buried therein. The slider 240 is guided in the guide groove 235 in such a manner that the fingertip cushion supporting surface 241 is slidable away from and toward the nail supporting surface 231. Generally, the nail supporting surface 231 is separated from the fingertip cushion supporting surface 241 by distance slightly smaller than the standard thickness of the fingertips inserted. A constant-load spiral spring 249 is accommodated in a recess formed in the slider 240. The inner end of the spiral spring 249 is pressed onto a rotary shaft 248 rotatably mounted on the slider by virtue of the elasticity thereof, and an outer end 249a is fixed to the fingertip supporting base 230.

As the slider 240 lowers during the measurement, the constant-load spiral spring 249 is unwound, and this allows a fixed amount of pressure corresponding to the winding force of the spring to be applied to the fingertip with respect to variations in the slide stroke.

Figure 15:
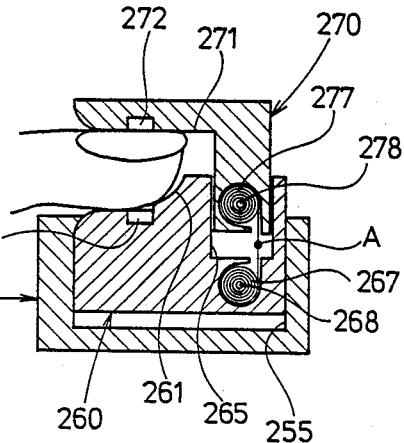
FIG. 15 is a cross-sectional view of the central portion of a fingertip pulse wave sensor, showing an eighth embodiment of the present invention.
Figure 16:
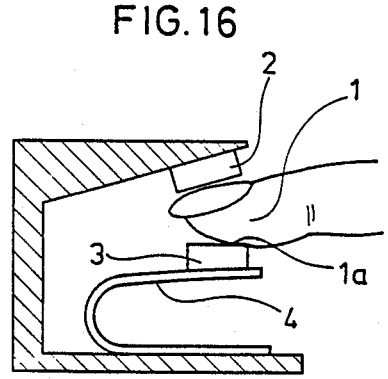
FIG. 16 is a cross-sectional view of a conventional fingertip pulse wave sensor.

FIG. 15 shows an eighth embodiment of the present invention. In this embodiment, a fingertip supporting base 250 has a guide groove 255 having a square cross-section, and a first slider 260 having a square cross-section is guided in this guide groove 255. The first slider 260 has a fingertip cushion supporting surface 261 with a light-emitting element 262 buried therein. The first slider 260 also has a guide groove 265, and a second slider 270 having a square cross-section is guided in this guide groove 265 in such a manner as to be slidable away from and toward the fingertip cushion supporting surface 261. The second slider 270 has a nail supporting surface 271 with a light-receiving element 272 buried therein. Constant-load spiral springs 267 and 277 are accommodated in recesses formed in the sliders 260 and 270, respectively. The inner ends of the spiral springs 267 and 277 are respectively pressed onto rotary shafts 268 and 278 rotatably supported on the sliders 260 and 270, and the outer ends thereof are fixed to the fingertip supporting base 250 at point A.

During the measurement, the slider 260 lowers while the slider 270 rises by distances corresponding to the thickness of the fingertips inserted. At this time, the constant-load spiral springs 267 and 277 are unwound, and this allows a constant amount of pressure to be applied to the fingertip with respect to the variations in the slide stroke. It also allows fingertips having various thickness to be inserted between the sliders 260 and 270 in a stable conditon.

What is claimed is:

1. A fingertip pulse wave sensor, comprising:
   a fingertip supporting base having a fingertip cushion supporting surface on which a fingertip cushion is set;
   a slider having a nail contact surface which is disposed in opposed relationship with said fingertip cushion supporting surface at an interval smaller than the standard thickness of fingertips inserted, said slider being guided on said fingertip supporting base in such a manner as to be slidable in the direction in which said nail contact surface is moved away from or toward said fingertip cushion supporting surface;
   an elastic body for urging said slider in the direction in which said nail contact surface is moved toward said fingertip cushion supporting surface, in such a manner that said elastic body applies a substantially fixed amount of pressure to said slider with respect to variations in the slide stroke caused by variations in the position of said nail contact surface where it makes contact with a nail; and
   a light-emitting element disposed in either of said fingertip cushion supporting surface and said nail contact surface and a light-receiving element disposed in the other of said fingertip cushion supporting surface and said nail contact surface in opposed relationship with said light-emitting element.

2. A fingertip pulse wave sensor according to claim 1, wherein said fingertip supporting base has a rising surface which includes said fingertip cushion supporting surface and a fingertip guide surface with continues from said fingertip cushion supporting surface, said fingertip cushion supporting surface and said fingertip guide surface being slanted so as to cope with the standard shape of the fingertip cushion of a finger resting in a relaxed state and that of the finger cushion of the finger located between the first and second joints, respectively.

3. A fingertip pulse wave sensor according to claim 1, wherein said fingertip cushion supporting surface has a recess or a hole through which the central portion of the fingertip cushion escapes, a light-emitting element or a light-receiving element being disposed behind said recess or said hole.

4. A fingertip pulse wave sensor according to claim 1, wherein said fingertip supporting base is formed integrally with a body of said sensor.

5. A fingertip pulse wave sensor, comprising:
   a fingertip supporting base having a rising surface which includes a fingertip cushion supporting surface and a fingertip guide surface which continues from said fingertip cushion supporting surface, said fingertip cushion supporting surface and said fingertip guide surface being slanted with respect to a bottom surface of said fingertip supporting base so as to cope with the standard shape of a fingertip cushion of a finger resting in a relaxed state and that of the finger cushion of said finger between the first and second joints, respectively;
   a slider having a nail contact surface which is disposed in opposed relationship with said fingertip cushion supporting surface at an interval slightly smaller than the standard thickness of a fingertip, said slider being guided on said fingertip supporting base in such a manner as to be slidable slantingly with respect to said bottom surface so that said nail contact surface can be moved away from or toward said fingertip cushion supporting surface;
   a constant-load spiral spring accommodated in said fingertip supporting base, an inner end of said constant-load spiral spring being rotatably supported on said slider or said fingertip supporting base and an outer end thereof being connected to said fingertip supporting base or said slider so as to allow said slider to be urged against the separation thereof; and
   a light-emitting element disposed in either of said fingertip cushion supporting surface and said nail contact surface and a light-receiving element disposed in the other of said fingertip cushion supporting surface and said nail contact surface.

6. A fingertip pulse wave sensor, comprising:
   a fingertip supporting base having a nail supporting surface;
   a slider having a fingertip cushion supporting surface which is disposed in opposed relationship with said nail supporting surface at an interval smaller than the standard thickness of fingertips, said slider being guided on said fingertip supporting base in such a manner as to be slidable in the direction in which said slider is moved away from or toward said nail supporting surface;
   an elastic body for urging said slider in the direction in which said slider is moved toward said nail supporting surface in such a manner that the pressure applied by said elastic body becomes substantially constant with respect to variatons in the slide stroke of said slider in the direction in which said fingertip cushion supporting surface is moved away from said nail supporting surface when a fingertip is held on said fingertip cushion supporting surface; and a light-emitting element disposed in either of said fingertip cushion supporting surface and said nail contact surface and a light-receiving element disposed in the other of said fingertip cushion supporting surface and said nail contact surface.

7. A fingertip pulse wave sensor according to claim 6, wherein said nail supporting surface is formed on said fingertip supporting base or a second slider guided on a first slider having said fingertip cushion supporting surface, and said second slider is also urged by an elastic body which is capable of applying a substantially fixed amount of pressure with respect to variations in the slide stroke.

* * * * *